US010420609B2

(12) United States Patent
Tang

(10) Patent No.: US 10,420,609 B2
(45) Date of Patent: Sep. 24, 2019

(54) MEDICAL DEVICE AND METHODS OF USE

(71) Applicant: Boston Scientific Scimed, Inc., Maple Grove, MN (US)

(72) Inventor: Yushen Tang, Shanghai (CN)

(73) Assignee: Boston Scientific Scimed, Inc., Maple Grove, MN (US)

( * ) Notice: Subject to any disclaimer, the term of this patent is extended or adjusted under 35 U.S.C. 154(b) by 189 days.

(21) Appl. No.: 15/233,773

(22) Filed: Aug. 10, 2016

(65) Prior Publication Data

US 2017/0215963 A1 Aug. 3, 2017

(30) Foreign Application Priority Data

Jan. 29, 2016 (CN) .......................... 2016 1 0064828

(51) Int. Cl.
| | |
|---|---|
| *G01N 21/00* | (2006.01) |
| *A61B 18/22* | (2006.01) |
| *A61B 90/00* | (2016.01) |
| *A61B 18/00* | (2006.01) |
| *A61N 5/06* | (2006.01) |
| *A61N 5/067* | (2006.01) |

(52) U.S. Cl.
CPC .............. *A61B 18/22* (2013.01); *A61B 90/06* (2016.02); *A61B 90/08* (2016.02); *A61B 2018/00005* (2013.01); *A61B 2018/00779* (2013.01); *A61B 2090/0803* (2016.02); *A61N 2005/063* (2013.01); *A61N 2005/067* (2013.01); *A61N 2005/0626* (2013.01)

(58) Field of Classification Search
CPC ...... A61N 2005/0626; A61N 2005/063; A61N 2005/067; A61B 18/22; A61B 2018/00005; A61B 2018/00779; A61B 2090/0803; A61B 90/06; A61B 90/08
USPC ........................................................ 356/73.1
See application file for complete search history.

(56) References Cited

U.S. PATENT DOCUMENTS

| | | | |
|---|---|---|---|
| 4,883,054 A | 11/1989 | Fuller et al. | |
| 5,455,672 A | 10/1995 | Lamonde et al. | |
| 5,569,240 A | 10/1996 | Dowlatshahi et al. | |
| 2003/0174309 A1* | 9/2003 | Dewey .................. | A61B 18/20 356/73.1 |
| 2007/0139924 A1 | 6/2007 | Easley et al. | |
| 2009/0149845 A1 | 6/2009 | Brown | |

(Continued)

FOREIGN PATENT DOCUMENTS

| | | |
|---|---|---|
| CN | 103054588 A | 4/2013 |
| CN | 103983424 A | 8/2014 |
| WO | WO 01/11331 A1 | 2/2001 |

OTHER PUBLICATIONS

International Search Report and Written Opinion for International Application No. PCT/US2016/055357, dated Dec. 16, 2016 (10 pages).

(Continued)

*Primary Examiner* — Sunghee Y Gray
(74) *Attorney, Agent, or Firm* — Bookoff McAndrews, PLLC

(57) ABSTRACT

The present disclosure is directed to a medical device. More particularly, aspects of the disclosure relate to a medical device including an energy source configured to emit energy into a first end of an optical fiber and a monitoring device configured to receive energy from a second end of the optical fiber.

20 Claims, 5 Drawing Sheets

(56) References Cited

U.S. PATENT DOCUMENTS

| | | | |
|---|---|---|---|
| 2010/0215358 A1* | 8/2010 | Harres | G01R 31/1227 398/17 |
| 2011/0160713 A1* | 6/2011 | Neuberger | A61B 18/22 606/15 |
| 2013/0102861 A1 | 4/2013 | Oki et al. | |
| 2014/0194693 A1 | 7/2014 | Imaizumi et al. | |

OTHER PUBLICATIONS

Laser Power Meter and Laser Energy Meters | Gentec-EO. www.gentec-eo.com/ as of Sep. 2, 2015.

Laser Power Meter | Infrared optics | co2 laser optics—Ophir Laser Measurement. www.ophiropt.com/ as of Sep. 2, 2015.

Chinese Office Action for Chinese Application No. 201610064828.2, dated Oct. 9, 2018 (15 pages).

* cited by examiner

MEDICAL DEVICE AND METHODS OF USE

FIELD OF THE DISCLOSURE

Examples of the present disclosure relate generally to any medical device using fibers to transmit energy, including laser energy from a laser. More particularly, aspects of the disclosure relate to testing an optical fiber to determine its efficiency or whether it may be used for additional procedures. Aspects of the disclosure also cover methods of using such devices with various medical devices.

BACKGROUND OF THE DISCLOSURE

Many medical devices use optical fibers to transmit laser energy from a laser source and/or light from a light source. After each use, the efficiency of the optical fiber decreases and energy provided to the proximal end of the optical fiber may not result in as much energy transmitted to the distal end as previous uses. As a result, operators often replace an optical fiber after a certain number of uses (e.g., ten uses) or certain amount working time (e.g., fifteen hours of working time). In some cases, the optical fiber is still sufficient for additional uses or use time, but the operator does not know whether or how many additional uses are still available. Replacing and discarding an optical fiber when it still has the ability to provide additional uses results in an additional costs to users and increased waste. As such, there exists a need for a testing device to test the efficiency of optical fibers and thus, reduce the cost and waste associated with optical fibers in medical devices.

SUMMARY OF THE DISCLOSURE

It is to be understood that both the foregoing general description and the following detailed description are exemplary and explanatory only and are not restrictive.

According to one aspect of the present disclosure, a medical device may include an energy source configured to emit energy into a first end of an optical fiber, and a monitoring device configured to receive energy from a second end of the optical fiber.

Additionally or alternatively, the medical device may include one or more other features describe here. For example, the energy source and the monitoring device may be disposed within a capital box of the medical device. The capital box may include a socket in a first surface of the capital box to provide access to the energy source. The capital box may include a testing hole in the first surface of the capital box to provide access to the monitoring device. The monitoring device may be a power meter. The at least one optical fiber may be a single fiber. The medical device may include a cooling system. The medical device may include a fiber fixture. The medical device may include an interface configured to receive a value of an emission power of energy emitted by the energy source. The energy source may be a laser. The laser may emit energy at approximately 5 W. The monitoring device may determine power of the energy emitted through the second end of the optical fiber. The medical device may include a processor configured to execute the instructions to compare the power of the energy emitted from the laser and the energy emitted from the second end of the optical fiber. The monitoring device may be disposed on a top surface of the medical device. The height of the monitoring device may be adjustable.

According to another aspect of the present disclosure, a method may include inserting a second end of an optical fiber into a testing hole of a monitoring device, wherein the first end of the optical fiber is positioned to receive energy emitted from an energy source, instructing the energy source to emit energy at a certain power, measuring the power of the energy emitted from the second end of the optical fiber, and determining whether the difference between the power of the energy emitted by the energy source and the power of the energy emitted from the second end of the optical fiber is within a certain threshold.

Additionally or alternatively, the method may include one or more other features describe here. For example, the threshold may be five percent. The method may include displaying the measured power of the energy emitted from the second end of the optical fiber on an interface.

According to another aspect of the present disclosure, medical device, may include a capital box, including at least one opening in at least one surface of the capital box providing access to an interior of the capital box, a laser disposed within the capital box, a power meter disposed within the capital box, and an optical fiber including a first end and a second end, wherein the optical fiber is configured to received laser energy from the laser through the first end and emit laser energy through the second end Additionally or alternatively, the medical device may include one or more other features describe here. For example, the medical device may include a processor, wherein the power meter is configured to determine a receipt value related to the energy emitted from the second end and the processor is configured to instruct the laser to emit energy at a certain emission value and determine the difference between the determined receipt value and the instructed emission value.

BRIEF DESCRIPTION OF THE DRAWINGS

The accompanying drawings, which are incorporated in and constitute a part of this specification, illustrate various exemplary aspects and together with the description, serve to explain the principles of the disclosed examples.

DETAILED DESCRIPTION

Reference will now be made in detail to examples of the disclosure, examples of which are illustrated in the accompanying drawings. Wherever possible, the same reference numbers will be used throughout the drawings to refer to the same or like parts. As used herein, the terms "about," "substantially," and "approximately," may indicate a range of values within +/−5% of a stated value.

Aspects the present disclosure relate generally to any medical device that uses optical fibers to transmit energy, including laser energy from a laser and light from a light source, e.g., an LED. Examples of medical devices transmitting energy via optical fiber(s) includes laser therapy medical devices. Aspects of the disclosure relate to a monitoring device for testing an optical fiber to determine its efficiency. Aspects of the disclosure also cover methods of using such monitoring devices with various medical devices.

Figure 1:
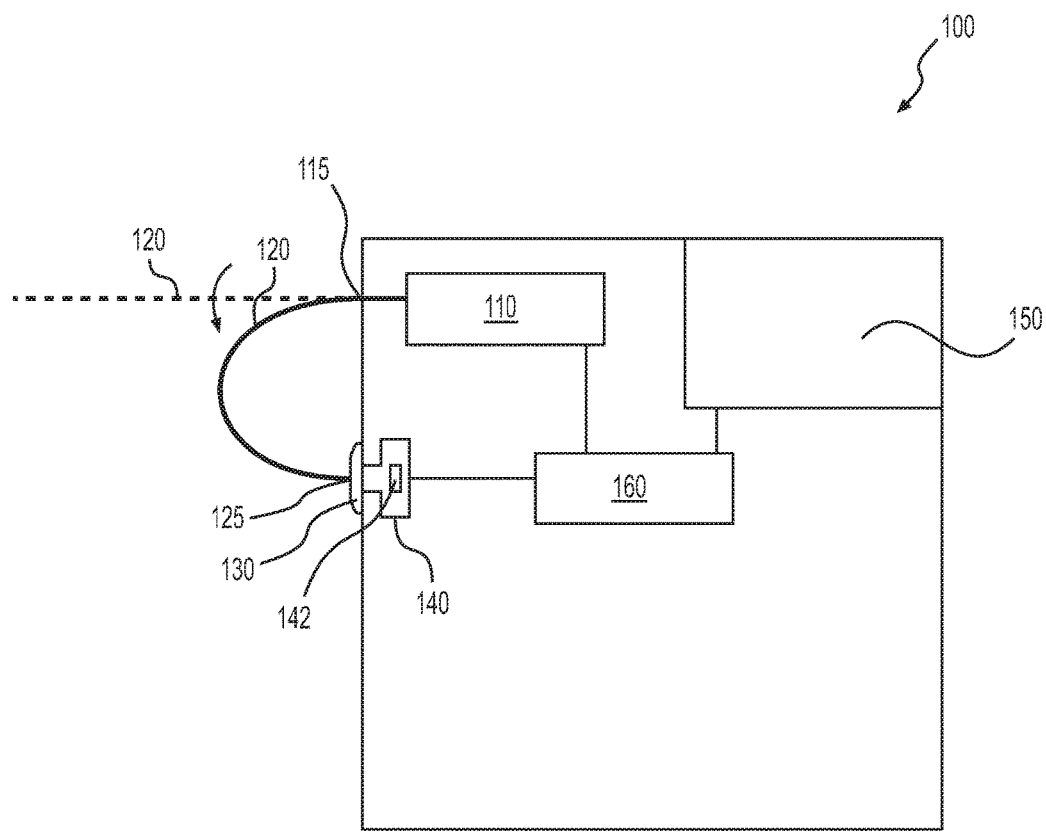
FIG. 1 illustrates a side view of an exemplary medical device, including an optical fiber, a monitoring device, and an integrated display screen.

FIG. 1 illustrates a front view a medical device including one of such monitoring device 140, e.g., a power meter. The medical device may include a capital box 100. Capital box 100 may include an energy source 110, a socket 115, an optical fiber 120, a testing hole 125, receptacle 130, a monitoring device 140, an interface 150, and/or a controller 160.

In some examples, energy source 110 may be disposed within the capital box 100. In other examples, energy source 110 may be separate from, but connected to capital box 100. Energy source 110 may be a laser source and/or a light source. The energy source may be a light source for transmitting visible light through an optical fiber. The energy source may be a laser source for transmitting laser energy through an optical fiber, such as, e.g., a holmium (Ho) laser source, a holmium:YAG (Ho:YAG) laser source, a neodymium-doped:YAG (Nd:YAG) laser source, a semiconductor laser diode, a potassium-titanyl phosphate crystal (KTP) laser source, a carbon dioxide (CO2) laser source, an Argon laser source, an Excimer laser source, a diode laser source, or another suitable laser source. In some examples, the laser source may be a laser diode. In some examples, a high power (e.g., superluminescent) LED may be used in place of a laser source. In some examples, an intense, pulsed light source may be used in place of a laser source.

Carbon dioxide laser sources may be utilized in medical devices providing tissue ablation with minimal bleeding. Argon laser sources may be utilized in medical devices providing tissue ablation at short depth. Nd:YAG laser sources may be used in medical devices providing deeper depth of penetration into tissue. Excimer laser sources may be used in medical devices designed to remove very fine layers of tissue with little heating of surrounding tissue.

Energy source 110 may emit energy in any known pattern, including a single emission and/or pulse energy. The numerical aperture of energy emitted from the energy source 110 may be any suitable numerical aperture, including between approximately 0.1 and approximately 0.4. The energy may be associated with a range of electromagnetic radiation from an electromagnetic radiation spectrum. In some embodiments, the produced energy may be in a wavelength from about 300 nm to about 2100 nm, or may be another suitable wavelength. The energy may be emitted at any power, including but not limited to between approximately 2.5 W and approximately 10 W, or approximately 5 W.

As shown in FIG. 1, socket 115 may be located on a first surface of capital box 100. Socket 115 may allow a first end of optical fiber 120 to access the interior of capital box 100 and align with an internally disposed energy source 110. Optical fiber 120 may be configured to receive optical energy emitted (i.e., launched) from energy source 110. Energy may be propagated through optical fiber 120 until the energy is transmitted from a second end, for example, away from energy source 110 and into monitoring device 140 at sensor 142. That is, optical fiber 120 may act as a waveguide for the energy. Sensor 142 may be any sensor known in the art, including a standard thermal sensor, photodiode, or pyroelectric types. In some examples, sensor 142 may receive the laser waveform emitted from laser fiber 120 and transfer the light wave to thermal energy. The thermal energy may then be transferred to an electrical signal for power measurement. The power value measurement may then be sent to a processor (e.g. a processor within controller 160) through, for example, an RS232 or a USB. Once received by controller 160, the measured output power may be compared to the emitted power. In some examples, as described in further detail below, the measured output power may be displayed on display 490 of FIG. 4 in output section 470.

In some embodiments, optical fiber 120 may be any optical fiber known in the art. For example, optical fiber 120 may be a silica-based optical fiber and may include, for example, a fiber core, one or more cladding layers (e.g., a cladding layer disposed around the fiber core), a buffer layer (e.g., a buffer layer disposed around a cladding layer), and/or a jacket (e.g., a jacket disposed around a buffer layer). However, optical fiber 120 may additionally or alternatively include other suitable materials, and may be formed in other suitable configurations.

In some examples, the fiber core of optical fiber 120 may be formed of a suitable material for the transmission of energy from energy source 110. In some examples, for example, the fiber core may be formed of silica with a low hydroxyl (OH—) ion residual concentration, or may be formed of another suitable material. The fiber core may be a multi-mode fiber core and can have a step or graded index profile. The fiber core may also be doped with a concentration of a dopant (e.g., an amplifying dopant).

As shown in dashed lines in FIG. 1, optical fiber 120 may extend and/or loop back so that the second end of optical fiber 120 may be inserted into a testing hole 125 of receptacle 130. Receptacle 130 may assist an operator in inserting laser fiber 120 into testing hole 125. Testing hole 125 of receptacle 130 may receive the second end of the optical fiber 120 and may align it with the monitoring device, e.g., so that energy is emitted onto sensor 142 of power meter 140. Sensor 142 may be configured to monitor any output of optical fiber 120, including, but not limited to wavelength and power. Receptacle 130 may be one of more discs stacked axially of each other and may protrude from monitoring device 140 and capital box 100. In some examples, like those illustrated in FIG. 2, receptacle 130 may have an outermost surface flush with a surface of capital box 100 or within a recess within a surface of capital box 100. In the example illustrated in FIG. 1, receptacle 130 are positioned below socket 115 on the first surface of capital box 100 (e.g., the same surface as socket 115 is located). Capital box 100 and testing hole 125 of receptacle 130 are not limited to these positions. For example, receptacle 130 may be above, lateral, or diagonal of socket 115. In other examples, receptacle 130 may not be on the first surface, for example, receptacle 130 may be on any side surface or the top surface of capital box 100. In addition to or as an alternative to testing hole 125 and/or receptacle 130, the second end of optical fiber 120 may be connected to and/or aligned with monitoring device 140 in any way, including, but not limited to the exemplary fiber fixture described in further detail below with respect to FIG. 5.

Figure 2:
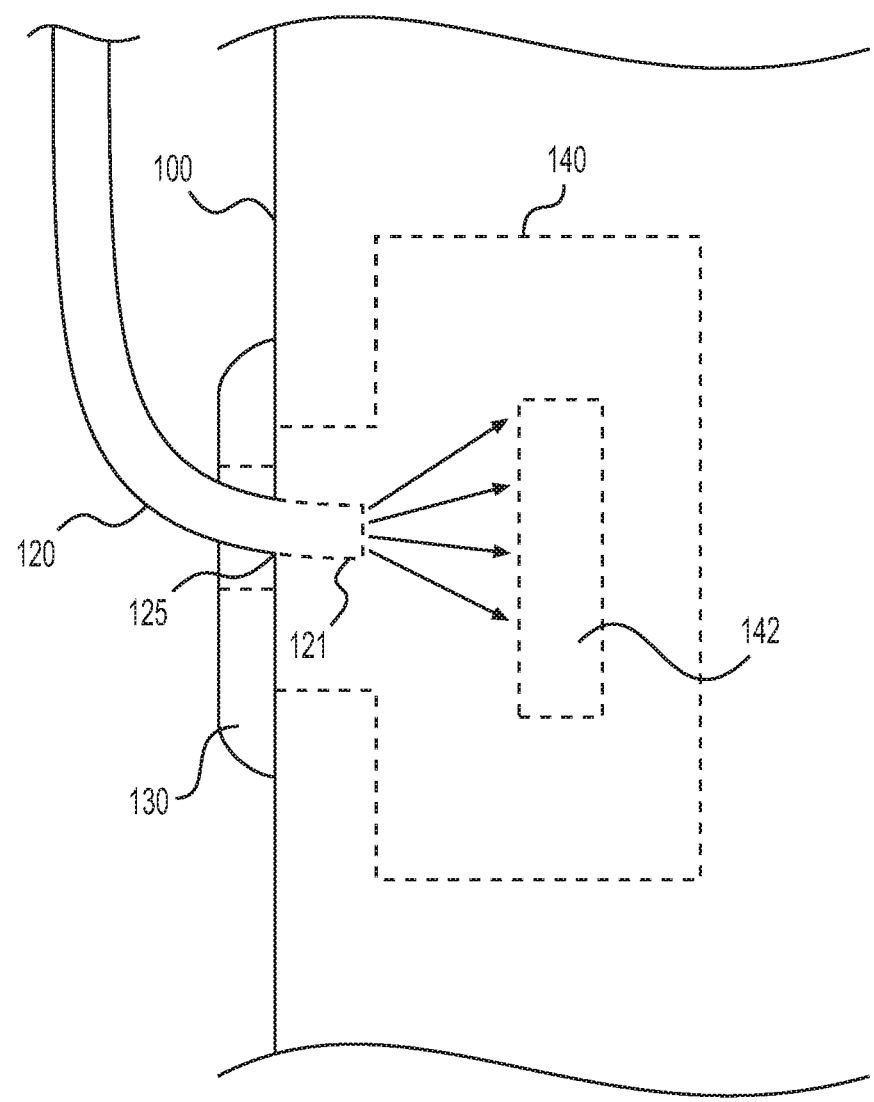
FIG. 2 illustrates an enlarged excerpt of capitol box 100.

FIG. 2 is an enlarged excerpt of capitol box 100. As shown in FIG. 2, the second end 121 of optical fiber 120 may be inserted through testing hole 125 and into monitoring device 140. As illustrated by the arrows in FIG. 2, energy, e.g., as emitted from an energy source (e.g., energy source 110 of FIG. 1 into a first end of optical fiber 120), may be emitted through the second end 121 of optical fiber 120 onto sensor 142.

As shown in FIG. 1, controller 160 may be coupled to energy source 110, monitoring device 140, and/or interface 150. In some implementations, controller 160 may include, for example and without limitation, a processor and memory. The memory may include any type of random access memory (RAM) or read-only memory (ROM) embodied in a physical storage medium, such as magnetic storage including floppy disk, hard disk, or magnetic tape; semiconductor storage such as solid state disk (SSD) or flash memory; optical disc storage; cloud storage; Digital Imaging and Communications in Medicine (DICOM) compatible storage; or magneto-optical disc storage. Software may include one or more applications and an operating system. According to one aspect, the memory may store processor-readable instructions, such as instructions for initiating energy transmission, monitoring received energy through optical fiber 120, processing received information, and/or displaying information to an operator. The processor may execute those instructions to perform one or more method steps.

Controller 160 may control and/or allow an operator to control the operation of various components of the medical device. For example, controller 160 may be configured to control (e.g., set, modify) a timing, a wavelength, and/or a power of the emitted energy from energy source 110. In some examples, controller 160 may also be configured to perform various functions of the medical device such as, e.g., laser selection, filtering, temperature compensation, and/or Q-switching.

Controller 160 (or the processor within controller 160) may also perform a variety of tasks depending on the nature of medical device such as generating images of the region of interest and/or communicating data processed by the processor within controller 160 to interface 150. Controller 150 (or the processor within controller 150) may communicate any information to interface 150 in any way. Such communication may include information related to received signals and/or processed signals.

As shown in FIG. 1, controller 160 (or the processor within controller 160) may be connected to interface 150. Interface 150 may be disposed within the same unit as controller 160, e.g., capital box 100 (FIG. 1) or in a separate, but connected unit. The interface 150 may communicate to controller 160 (or the processor within controller 160) input commands from an operator, including commands used to control and/or provide data to controller 160 and/or energy source 110. Interface 150 may include user input device(s), including but not limited to any type or combination of input/output devices, such as a display monitor, touchpad, touchscreen, microphone, camera, keyboard, and/or mouse. In some examples, interface 150 and controller 160 may be a single unit, for example, a tablet, a smartphone, and/or a personal computer. Interface 150 may include a display screen for output to an operator. The display screen may display, for example, output from the monitoring device 140. FIG. 4 illustrates an exemplary display/touchscreen 490 allowing an operator to input commands to controller 160 and a display of a numerical value representing a measured output (e.g., wavelength or power) received by the monitoring device 140 through optical fiber 120. For example, output section 470 may display, for example, a value received from controller 160 (or a processor within controller 160) as determined by monitoring device 140 of FIG. 1 and/or monitoring device 330 of FIGS. 3A and 3B. In some examples, the received value may be measured wavelength or power. Icons 472, 480, and/or 482 may be activated by the operator in any way including touching or pressing. When activated, status identification icon 472 may set the laser to a particular status, e.g., "ready" or "standby." Status output display 474 may display the status of the laser. As shown, the laser is "READY," but status output display 474 may indicate any status including "STANDBY," "LASER," "COMPLETE," etc. Work mode adjustment icons 482 may change the work mode of the laser. The laser may have any number of work modes known in the art including, as shown in FIG. 4, "CW" or "Continuous Wave." The current work mode setting may be displayed in work mode display 478. Power adjustment icons 480 may increase or decrease the power emitted into the first end of the laser fiber, e.g., number of watts. The current power setting may be displayed in power display 488.

The monitoring devices 140, 330 described herein may be any device known in the art and/or capable of determining whether an optical fiber is sufficiently efficient (e.g., by measuring output wavelength and/or power). In the example illustrated in FIG. 1, monitoring device 140 may be embedded and/or integral with a medical device (e.g., within capital box 100). FIG. 1 illustrates monitoring device 140 disposed within capital box 100 of the medical device. In some examples, the monitoring device may protrude partially out of a side surface (e.g., the first side surface that the socket 115 is positioned on) or may be affixed to a side surface of the capital box 100 of the medical device. In other examples, the monitoring device (e.g., monitoring device 330 of FIGS. 3A and 3B) may be configured to affix to a top surface of the capitol box 100 of the medical device.

Figure 3:
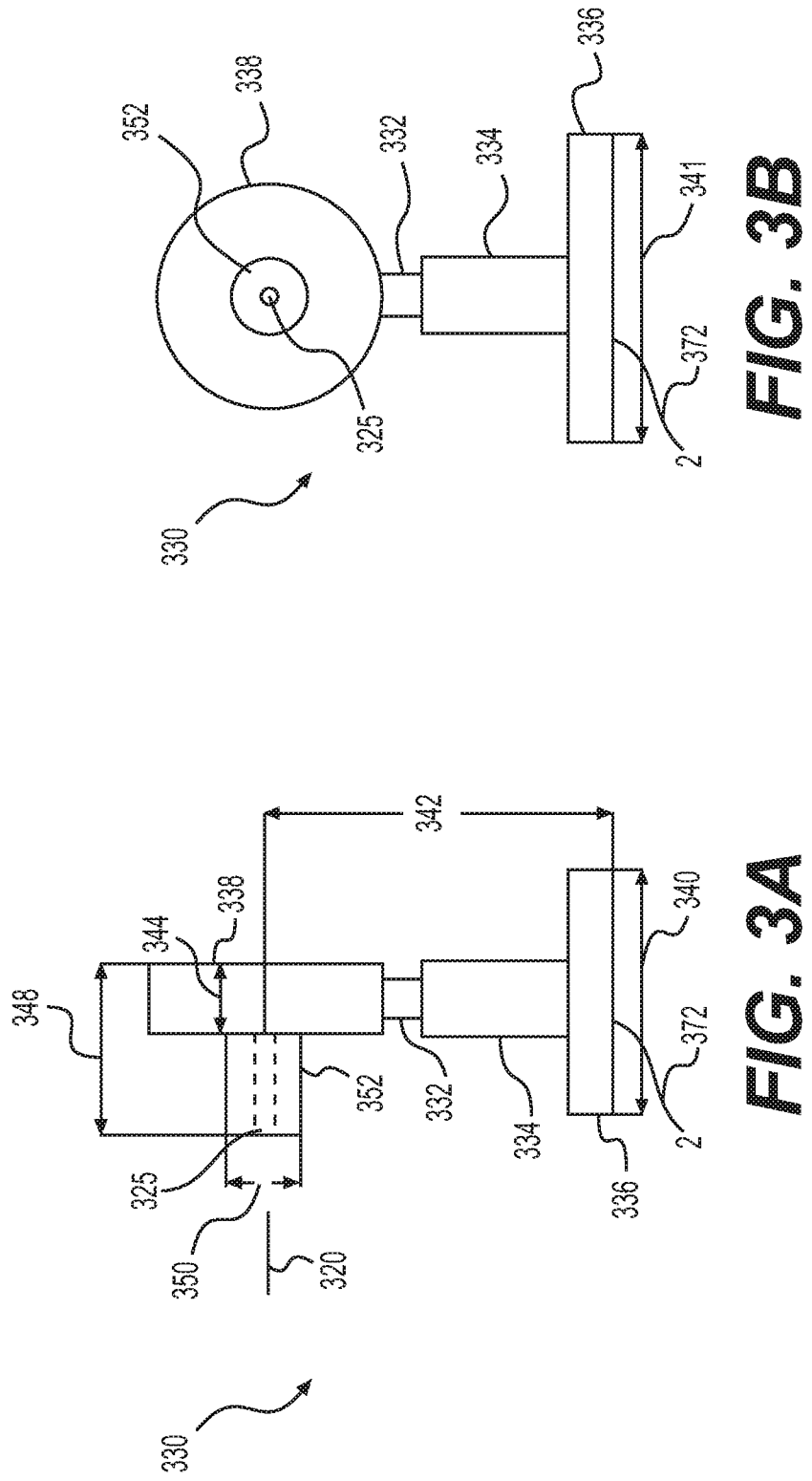
FIGS. 3A-B illustrate an exemplary front view and exemplary side view of a monitoring device with adjustable height for mounting on a medical device.
Figure 4:
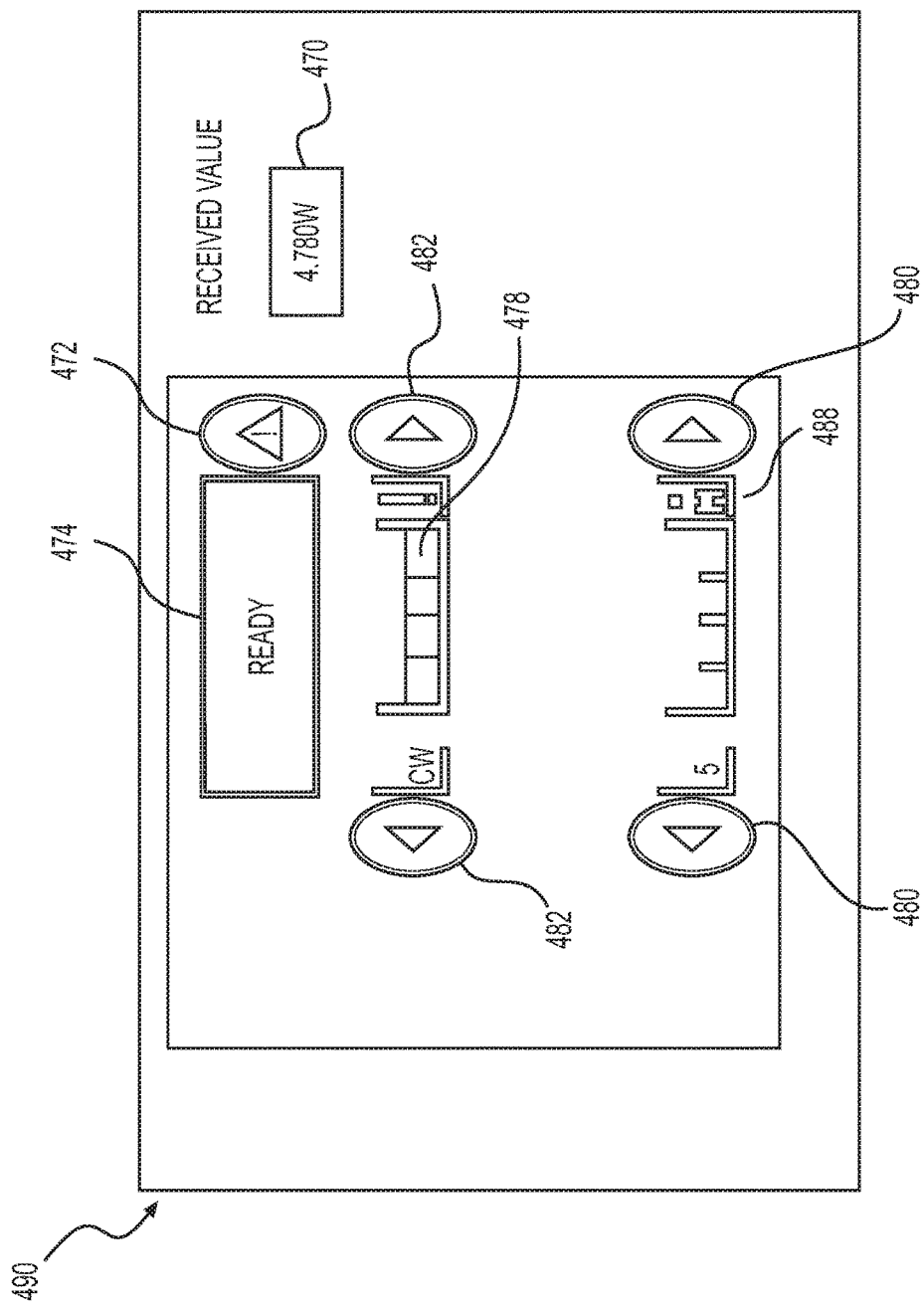
FIG. 4 illustrates an exemplary operator interface.

FIGS. 3A and 3B illustrate one such alternative exemplary monitoring device 330, in which the monitoring device 330 is configured to be completely external to a medical device and/or attach to a top surface of, for example, the capitol box 100 of the medical device. As shown in FIGS. 3A and 3B, monitoring device 330 may include absorber head 338, receptacle 352, testing hole 325, first support member 332, second support member 334, and platform 336. Absorber head 338 may be configured to measure some received numerical value related to the efficiency of optical fiber 320. Optical fiber 320 may enter testing hole 325 and may be aligned with various testing equipment within absorber head 338. Receptacle 352 may be one or more disc-shaped components traverse to and protruding from the central axis of absorber head 338.

Platform 336 may be configured to attach to a medical device, e.g., the top of capital box 100 of FIG. 1. For example, platform 336 may be generally flat, adapted to be fastened to a structure, such as, e.g., a medical device platform and/or capital box 100 of FIG. 1. The attachment of platform 336 to a structure may be accomplished with screws (not shown) or any conventional fastener, and appropriate holes may be provided within platform 336 for that purpose. Any other suitable attachment means may be used, however.

Second support member 334 may be substantially cylindrical. However, any shape may be used. Second support member 334 may be attached to platform 336. In some examples, second support member 334 and platform 336 may be fabricated from a one-piece construction. In other examples, second support member 334 and platform 336 may be discrete components that are secured to one another by any suitable fastening means, e.g., welding.

Second support member 334 may include a central bore. The bore may be substantially cylindrical as well, but may be any shape. As shown, second support member 334 may be traverse to and/or extend substantially perpendicularly away from platform 336. However, second support member 334 may be disposed at any angle relative to platform 336.

First support member 332 may be similar in shape to the central bore of second support member 334 and/or may be substantially cylindrical. However, any suitable shape and size may be used. First support member 332 may be slidably disposed with the central bore of second support member 334. First support member 332 may be attached to absorber head 338. In some examples, first support member 332 and absorber head 338 may be discrete components that are secured to one another by any suitable fastening means, including, for example, welding.

Monitoring device 330 may communicate with a controller and/or interface (e.g., controller 160 of FIG. 1 and/or interface 150 of FIG. 1) in any way. For example, monitoring device 330 may communicate using wireless signals. In some examples, monitoring device 330 may communicate through wire 372. Wire 372 may start at absorber head 338. The wire may then exit absorber head 338 out a side surface or may extend through first support 332, second support 334, and, as shown in FIG. 3A, exit through the bottom surface of platform 336. The wire may then connect to a capital box (e.g., capital box 100), a controller (e.g., controller 160) and/or an interface (e.g., interface 150). In some examples, monitoring device 330 may include a controller and/or a processor. Such a controller and/or processor may instruct a sensor to measure various values, including, but not limited to wavelength and power. Such a controller and/or processor may process and/or analyze received energy and may communicate measured values to a second controller, processor, and/or an interface.

The height of absorber head 338 relative to platform 336 may, in some examples, be adjustable. For example, first support member 332 may be moved to various positions within second support member 334. The height may be adjusted for various reasons, including depending, in part, on the length of optical fiber 320 and/or the position of the energy source (e.g., energy source 110 of FIG. 1) relative to monitoring device 330.

Monitoring device 330 may be suitably dimensioned to fit the desired medical device. For example, as shown in FIG. 3A, absorber head 338 may have any suitable diameter and thickness. In some examples, the diameter of absorber head 338 may be between approximately 30 mm and approximately 50 mm. The thickness 344 of absorber head 338 may be between approximately 10 mm and approximately 20 mm. Platform 336 may have any suitable length 340 and width 341. For example, the length 340 of platform 336 may be between approximately 15 mm and approximately 25 mm. The width 341 of platform 336 may be between approximately 20 mm and approximately 35 mm. The height 342 of testing hole 325, as measured from the bottom of platform 336 to testing hole 325, may be any suitable height and may be adjustable. For example, at its lowest height, height 342 of testing hole 325 may be between approximately 80 mm and approximately 100 mm from the bottom of platform 336. At its highest, height 342 of testing hole 325 may be between approximately 140 mm and approximately 155 mm from the bottom of platform 336. The distance 348 from the free end of receptacle 352 to the opposite end of absorber head 338 may be any suitable distance, including between approximately 30 mm and approximately 50 mm. The diameter 350 of receptacle 352 may be any suitable diameter less than the diameter of absorber head 338, including between approximately 15 mm and approximately 30 mm.

In some examples, the monitoring device (e.g., monitoring device 140) may measure the attenuation of an optical fiber (e.g., optical fiber 120). For example, an operator may insert a free end of an optical fiber (e.g., the second end of optical fiber 120) and may input a command into interface 150 to transmit an energy at a predetermined wavelength. The interface 150 may communicate this command to controller 160 (or a processor within controller 160), which may then instruct energy source 110 to transmit energy at the predetermined wavelength to the first end of optical fiber 120. The monitoring device may then measure/identify the wavelength of the energy transmitted through the second end of the optical fiber 120. The wavelength may be identified and/or processed by a processor within controller 160 and controller 160 may communicate that value to interface 150. This value may then be displayed at interface 150. Either the processor within controller 160 or an operator may then determine whether the wavelength measure at the second end of the optical fiber is within a certain threshold as the wavelength transmitted into the optical fiber by the energy source. In some examples, the threshold may be approximately ±5%.

In some examples, the monitoring device (e.g., monitoring device 140) may be measure the power in, for example, watts of an optical fiber (e.g., optical fiber 120). For example, an operator may insert a free end of an optical fiber (e.g., the second end of optical fiber 120) into a monitoring device (e.g., testing hole 325 of monitoring device 330) and may input a command into interface 150 to transmit an energy at a predetermined power level. The interface 150 may communicate this command to controller 160 (or a processor within controller 160), which may then instruct energy source 110 to transmit energy at that wattage to the first end of optical fiber 120. The monitoring device may then measure/identify the watts of energy transmitted through the second end of the optical fiber 120. The watts may be identified and/or processed by a processor within controller 160 and controller 160 may communicate that value to interface 150. Either the processor within controller 160 or an operator may then determine whether the measured power at the second end of the optical fiber is within a certain threshold as the power transmitted into the optical fiber by the energy source. In some examples, the threshold may be approximately ±2.5% to approximately ±5%, or approximately −2.5% to approximately −5%. In some examples, once the second end of the optical fiber desired for testing is inserted into the monitoring device, an operator may instruct the energy source to produce energy so that the emission power is 5 W. For example, the operator may activate power adjustment icons 482 until power display 488 indicates 5 watts. The operator may then initiate the laser in any way known in the art, including an icon on display 490 and/or a footswitch (not shown) In examples where the threshold is ±5%, acceptable and/or efficient optical fibers emit between 4.75 W and 5.25 W through a second end into the monitoring device 140, 330 and an optical fiber that emits energy through a second end that is not within this window should be rejected/disposed/etc. For example, the monitoring device (e.g., a power meter) communicating with display 490 may determine the power received from the second end of the optical fiber is 4.780 W. Such an optical fiber output power is within the acceptable threshold and therefore, that optical fiber may be suitable for use, e.g., used a subsequent time.

The monitoring device of the medical device (e.g., monitoring device 140 of FIG. 1 and/or monitoring device 330 of FIGS. 3A and 3B) may be, for example, a power meter, including any known and/or suitable power meter. In some examples, the power meter may be a thermopiles, pyroelectrics, and/or photo detectors power meter. The power meter may have any suitable power range, including between approximately 1 µW and approximately 30 kW, or approximately 4 pW to 3 W. The power meter may have any suitable monitor accuracy including between approximately 0.25%±5 μV and approximately 0.50%±10 μV. The monitoring device 140, 330 may additionally or alternatively include an energy meter, including any known and/or suitable energy meter. The energy meter may have any energy range including between approximately 30 fJ and approximately 30 kJ. The energy member may have any monitor accuracy including between approximately ±0.5% and approximately ±1.5% or approximately ±1%.

Figure 5:
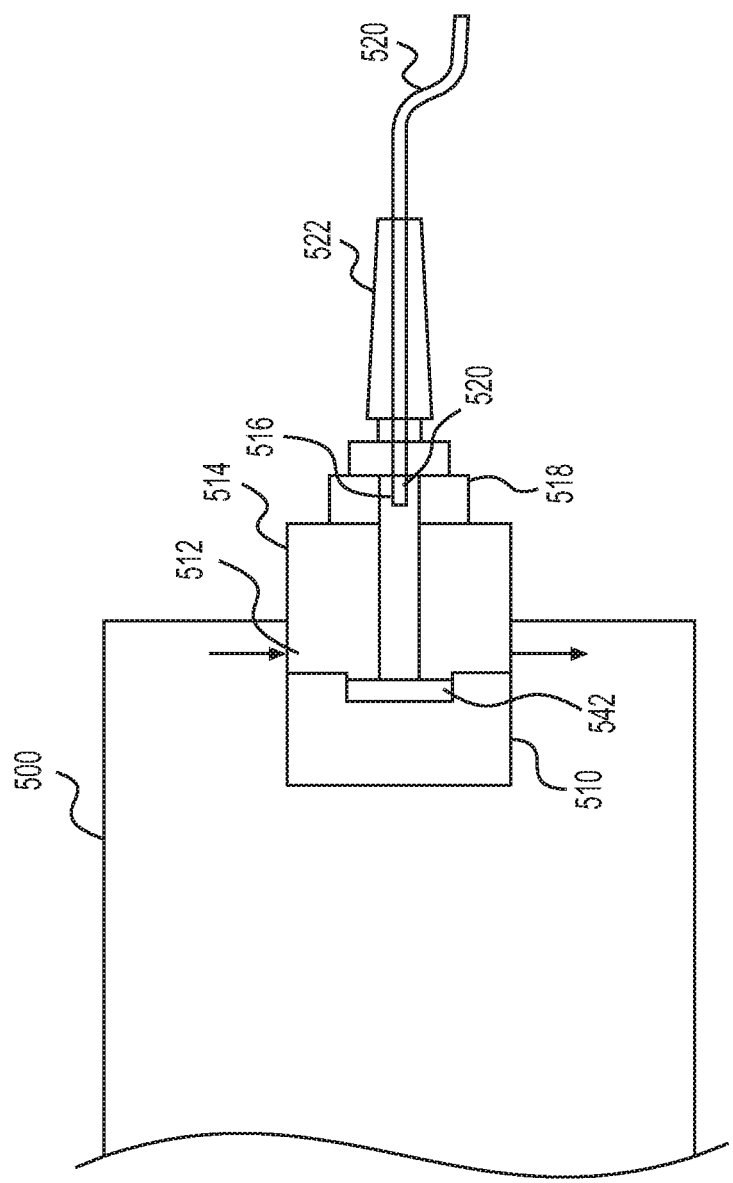
FIG. 5 illustrates an exemplary fiber fixture for securing an optical fiber to a monitoring device.

FIG. 5 illustrates an additional exemplary capital box with a fiber fixture. Some optical fibers may be flexible. In some examples, the optical fiber should be secured for engagement with a monitoring device. A monitoring device, a medical device including a monitoring device and/or a capital box in which a monitoring device is disposed may have any suitable fiber fixture, including but not limited to the fiber fixture of FIG. 5. For example, a capital box 500 of a medical device (similar to capital box 100 of FIGS. 1 and 2) may include an energy source (not shown), monitoring device 510, cooling system 512, receptacles 514 and 518, and/or channel 516. Fiber fixture 522 may be integral with receptacle 518 and/or may be removably attached to receptacle 518. In some examples, fiber fixture 522 includes a bore. The bore may be cylindrical with an opening on either end of fiber fixture 522 and may have a diameter sized to allow optical fiber 520 to be securely disposed within ft. A fiber fixture 522 may be integral with optical fiber 520 and/or removably attached. For example, prior to testing an optical fiber, an operator may slide optical fiber 520 into one end of fiber fixture 522 and extend the second end of optical fiber 520 beyond though the bore of fiber fixture 522, beyond the opposite end, and/or into channel 516. Channel 516 may extend through receptacles 514 and 518, cooling system 512 and terminate at monitoring device 510. Channel 516 may be configured to direct energy from the second end of optical fiber 520 to sensor 542 of monitoring device 510. Cooling system 512 may be any suitable cooling system. For example, cooling system 512 may be water cooled and/or air cooled. Cooling system 512 is illustrated in FIG. 5 with a cooling flow moving in a downward direction, but cooling system 512 is not limited thereto. For example, the cooling flow may be upward, circular, etc. Fiber fixture 522 may be made of any suitable material, including, for example, a plastic exterior and metal internal mechanical components.

The many features and advantages of the disclosure are apparent from the detailed specification, and thus, it is intended by the appended claims to cover all such features and advantages of the disclosure which fall within the true spirit and scope of the disclosure. Further, since numerous modifications and variations will readily occur to those skilled in the art, it is not desired to limit the disclosure to the exact construction and operation illustrated and described, and accordingly, all suitable modifications and equivalents may be resorted to, falling within the scope of the disclosure.

Other aspects of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device, comprising:
   an energy source configured to emit energy into a first end of an optical fiber, wherein the medical device is configured to emit energy of a first magnitude into the first end of the optical fiber; and
   a monitoring device configured to receive energy from a second end of the optical fiber, wherein the medical device is configured to measure the energy received from the second end of the optical fiber to determine a second magnitude, and
   wherein the medical device includes a processor that is configured to determine whether the second magnitude is within a five percent difference of the first magnitude.

2. The medical device of claim 1, wherein the energy source and the monitoring device are disposed within a capital box of the medical device.

3. The medical device of claim 2, wherein the capital box includes a socket in a first surface of the capital box to provide access to the energy source.

4. The medical device of claim 2, wherein the capital box includes a testing hole in the first surface of the capital box to provide access to the monitoring device.

5. The medical device of claim 1, wherein the monitoring device is a power meter.

6. The medical device of claim 1, wherein the at least one optical fiber is a single fiber.

7. The medical device of claim 1, further comprising:
   a cooling system.

8. The medical device of claim 1, further comprising:
   a fiber fixture.

9. The medical device of claim 1, further comprising:
   an interface configured to receive a value of an emission power of energy emitted by the energy source.

10. The medical device of claim 1, wherein the energy source is a laser.

11. The medical device of claim 10, wherein the laser emits energy at approximately 5 W.

12. The medical device of claim 1, wherein the monitoring device determines power of the energy emitted through the second end of the optical fiber.

13. The medical device of claim 12, wherein the processor is configured to execute instructions to compare the power of the energy emitted from the laser and the energy emitted from the second end of the optical fiber.

14. The medical device of claim 1, wherein the monitoring device is disposed on a top surface of the medical device.

15. The medical device of claim 1, wherein the height of the monitoring device is adjustable.

16. A method for monitoring a medical device, comprising:
   inserting a second end of an optical fiber into a testing hole of a monitoring device, wherein a first end of the optical fiber is positioned to receive energy emitted from an energy source;
   instructing the energy source to emit energy at a certain power;
   measuring the power of the energy emitted from the second end of the optical fiber;
   comparing the energy emitted at the certain power from the energy source into the first end of the optical fiber to the energy measured from the second end of the optical fiber to determine a difference between the power of the energy emitted by the energy source and the power of the energy emitted from the second end of the optical fiber; and
   determining whether the difference between the power of the energy emitted by the energy source and the power of the energy emitted from the second end of the optical fiber is less than five percent of the energy emitted at the certain power from the energy source into the first end of the optical fiber.

17. The method of claim 16, further comprising:
displaying the measured power of the energy emitted from the second end of the optical fiber on an interface.

18. The method of claim 17, further comprising, if the difference between the power of the energy emitted by the energy source and the power of the energy emitted from the second end of the optical fiber is less than the difference of five percent, using the optical fiber for a medical procedure.

19. A method, comprising:
inserting a first end of an optical fiber into a socket of a monitoring device to receive energy emitted from an energy source, wherein the optical fiber has been used in one or more medical procedures;
inserting a second end of an optical fiber into a testing hole of the monitoring device;
instructing the energy source to emit energy at a certain power;
measuring a power of the energy emitted from the second end of the optical fiber;
comparing the energy emitted at the certain power from the energy source into the first end of the optical fiber to the energy measured from the second end of the optical fiber to determine a difference between the power of the energy emitted by the energy source and the power of the energy emitted from the second end of the optical fiber; and
determining whether the difference between the power of the energy emitted by the energy source and the power of the energy emitted from the second end of the optical fiber is less than five percent of the energy emitted at the certain power from the energy source.

20. The method of claim 19, further comprising:
displaying the measured power of the energy emitted from the second end of the optical fiber on an interface; and
if the difference between the power of the energy emitted by the energy source and the power of the energy emitted from the second end of the optical fiber is less than five percent, using the optical fiber for a medical procedure.

* * * * *